United States Patent [19]
Freeman et al.

[11] Patent Number: 5,938,679
[45] Date of Patent: Aug. 17, 1999

[54] APPARATUS AND METHOD FOR MINIMALLY INVASIVE BLOOD SAMPLING

[75] Inventors: Dominique Freeman, Byron; Paul Lum, Los Altos; David King; Tad Simons, both of Palo Alto; Michael Greenstein, Los Altos, all of Calif.

[73] Assignee: Hewlett-Packard Company, Palo Alto, Calif.

[21] Appl. No.: 08/949,727

[22] Filed: Oct. 14, 1997

[51] Int. Cl.⁶ .................................................. A61B 17/14
[52] U.S. Cl. ........................................... 606/181; 606/183
[58] Field of Search .................... 606/181–185, 606/166, 169; 604/164

[56] References Cited

U.S. PATENT DOCUMENTS

| | | | |
|---|---|---|---|
| 2,061 | 4/1841 | Osdel . | |
| 1,135,465 | 4/1915 | Pollock . | |
| 3,030,959 | 9/1962 | Grunert | 128/329 |
| 3,046,987 | 7/1962 | Ehrlich | 128/314 |
| 3,358,689 | 12/1967 | Higgins | 128/329 |
| 3,712,293 | 1/1973 | Mielke, Jr. | 128/2 |
| 4,139,011 | 2/1979 | Benoit et al. | 128/329 |
| 4,203,446 | 5/1980 | Hofert et al. | 128/329 |
| 4,207,870 | 6/1980 | Eldridge | 128/766 |
| 4,230,118 | 10/1980 | Holman et al. | 128/314 |
| 4,442,836 | 4/1984 | Meinecke et al. | 128/314 |
| 4,449,529 | 5/1984 | Burns et al. | 128/314 |
| 4,469,110 | 9/1984 | Slama | 128/770 |
| 4,535,769 | 8/1985 | Burns | 128/314 |
| 4,577,630 | 3/1986 | Nitzsche et al. | 128/314 |
| 4,616,649 | 10/1986 | Burns | 128/314 |
| 4,624,253 | 11/1986 | Burns | 128/314 |
| 4,666,438 | 5/1987 | Raulerson | 604/272 |
| 4,677,979 | 7/1987 | Burns | 128/314 |
| 4,712,548 | 12/1987 | Enstrom | 128/314 |
| 5,057,082 | 10/1991 | Burchette, Jr. | 604/164 |
| 5,133,730 | 7/1992 | Biro et al. | 606/182 |
| 5,196,025 | 3/1993 | Ranalletta et al. | 606/182 |
| 5,211,652 | 5/1993 | Derbyshire | 606/182 |
| 5,266,359 | 11/1993 | Spielvogel | 427/388 |
| 5,304,347 | 4/1994 | Mann et al. | 422/67 |
| 5,318,583 | 6/1994 | Rabenau et al. | 606/182 |
| 5,318,584 | 6/1994 | Lange et al. | 606/182 |
| 5,342,382 | 8/1994 | Brinkerhoff et al. | 606/184 |
| 5,395,387 | 3/1995 | Burns | 606/181 |
| 5,462,533 | 10/1995 | Daugherty | 604/164 |
| 5,496,274 | 3/1996 | Graves et al. | 604/86 |
| 5,562,696 | 10/1996 | Nobles et al. | 606/185 |
| 5,571,132 | 11/1996 | Mawhirt et al. | 606/182 |
| 5,618,297 | 4/1997 | Hart et al. | 606/185 |
| 5,624,459 | 4/1997 | Kortenbach et al. | 606/185 |

FOREIGN PATENT DOCUMENTS

| | | | |
|---|---|---|---|
| 137 975A2 | 4/1985 | European Pat. Off. | A61B 5/14 |
| 0 449 147A2 | 8/1992 | European Pat. Off. | A61M 5/32 |

OTHER PUBLICATIONS

Letourneau et al., "Aspiration biopsy", pp. 8–29, General Considerations.

*Primary Examiner*—Michael Buiz
*Assistant Examiner*—Kevin Truong

[57] ABSTRACT

A blood sampling device for penetrating skin to obtain a blood sample is disclosed. The blood sampling device has a blade structure that can be extended from a housing to pierce the skin and then retracted. The blade structure has at least two blades each including a cutting edge. The blades abut one another to form a rigid joint from which the blades extend. The blades each have a distal portion in which the distance from the rigid joint to the cutting edge decreases towards and terminates at a sharp point at a distal end. Each blade generally forms an angle less than 180 degrees with at least one neighboring blade. This structure decreases the tendency of the blade structure to flex as the distal end of the blade structure penetrates the skin to yield blood.

22 Claims, 8 Drawing Sheets

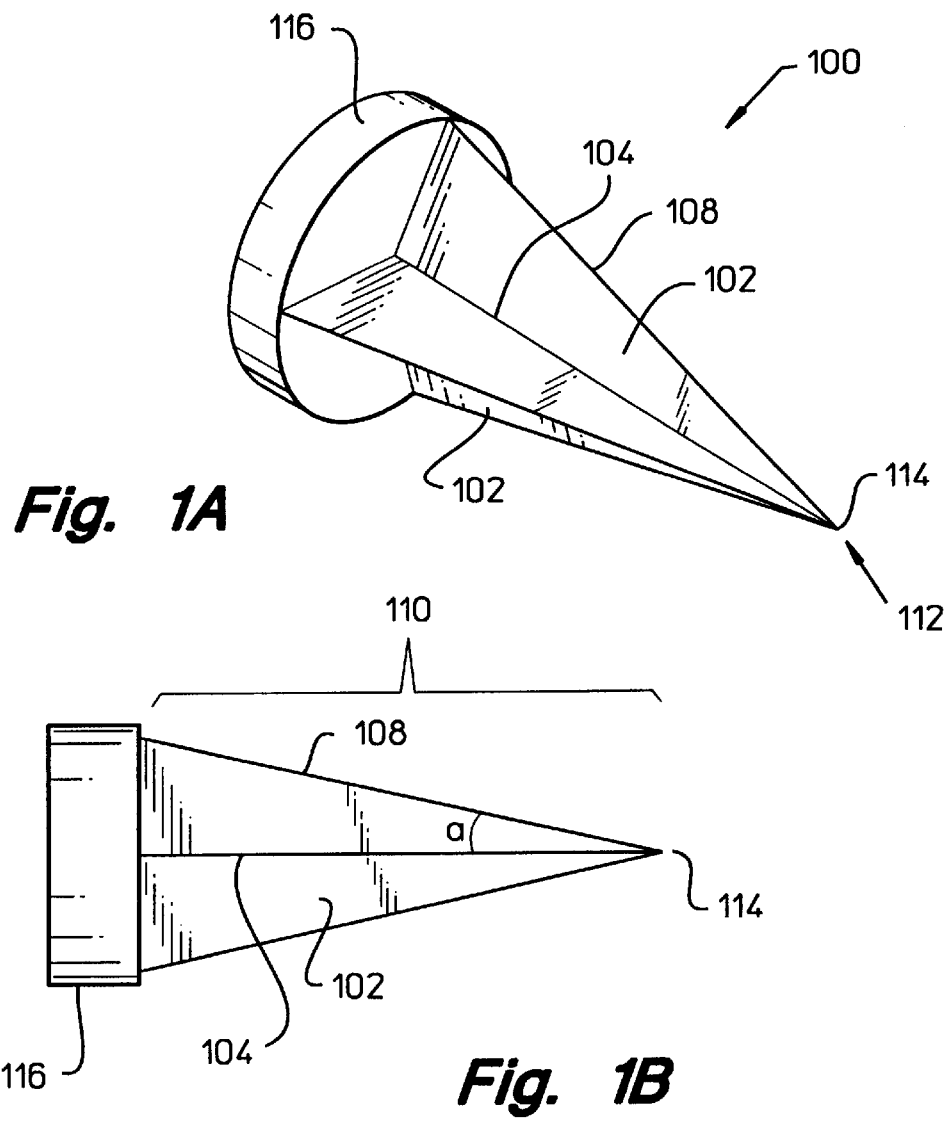
Fig. 1A
Fig. 1B
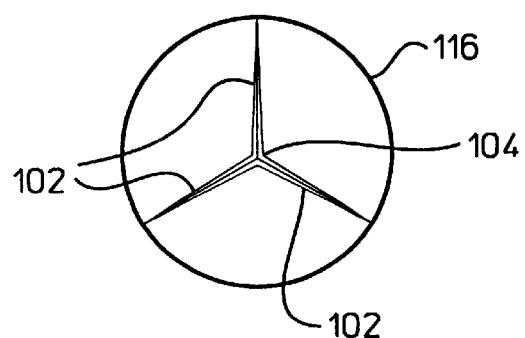
Fig. 1C

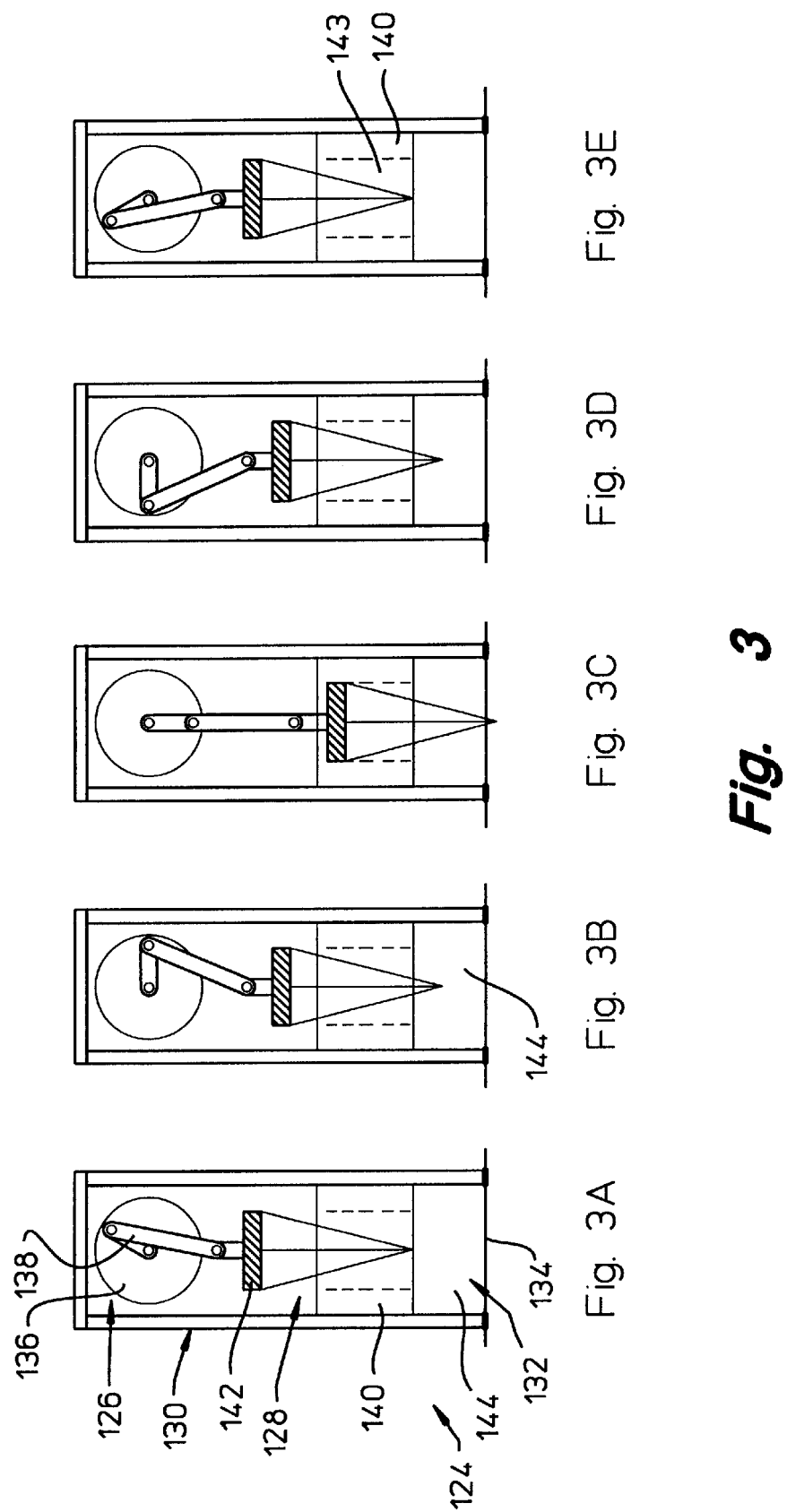

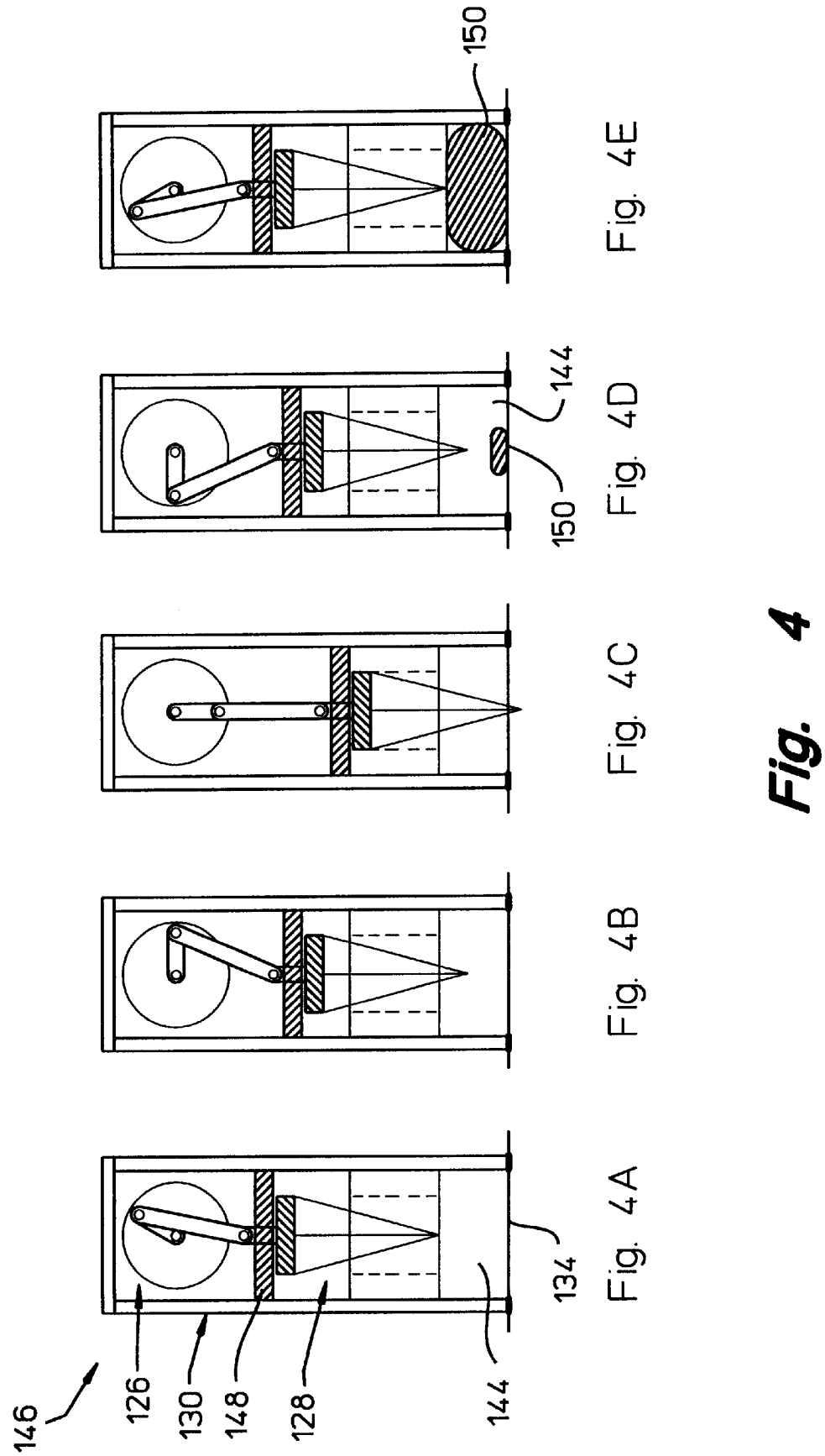

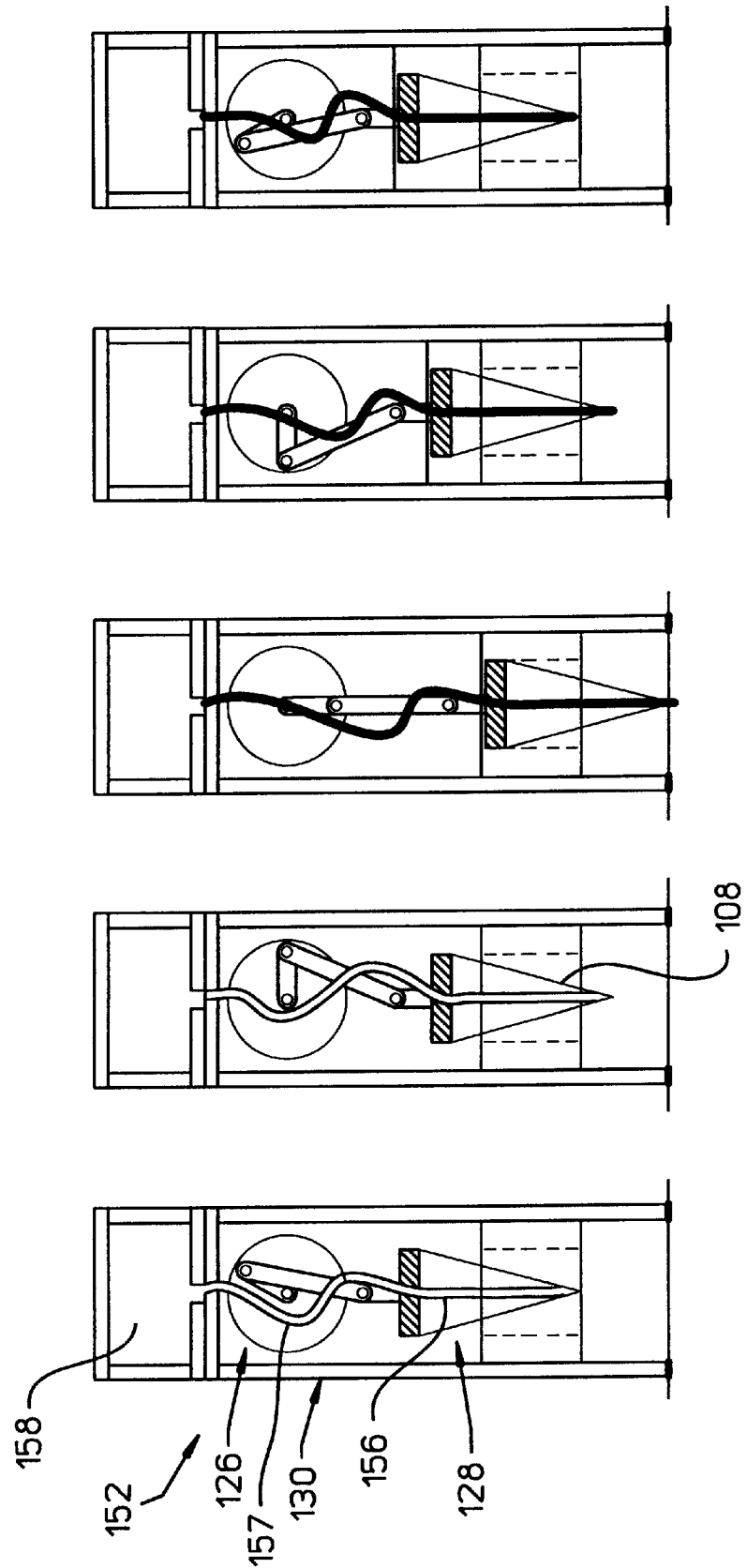

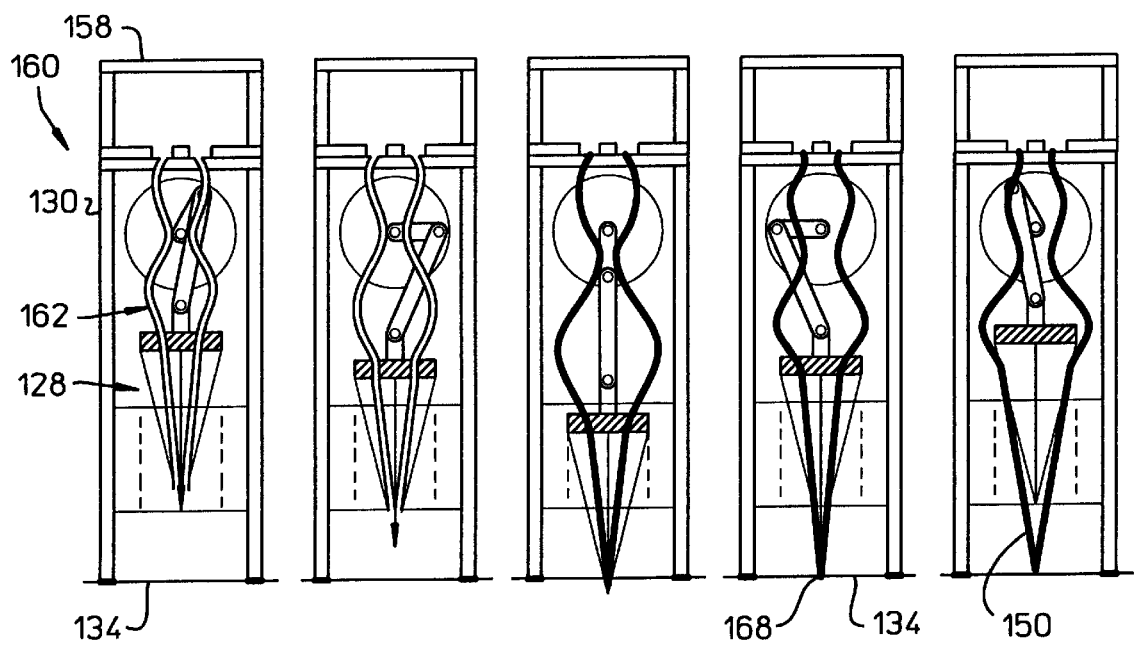
Fig. 6A   Fig. 6B   Fig. 6C   Fig. 6D   Fig. 6E
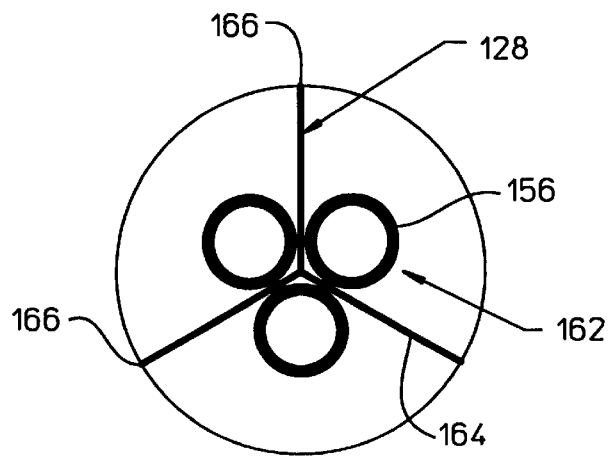
Fig. 6F
*Fig. 6*

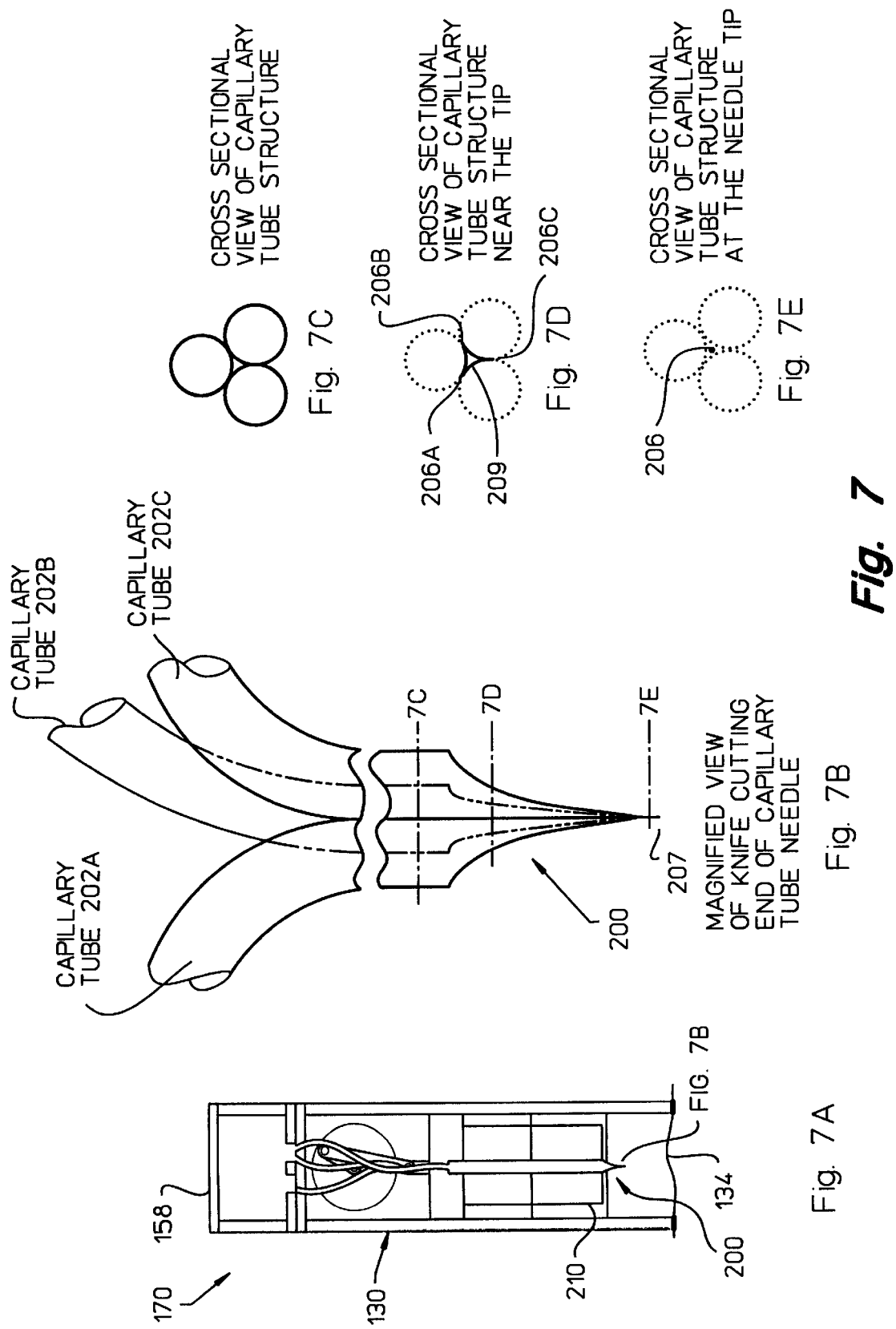

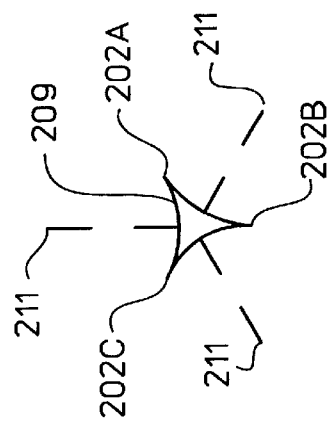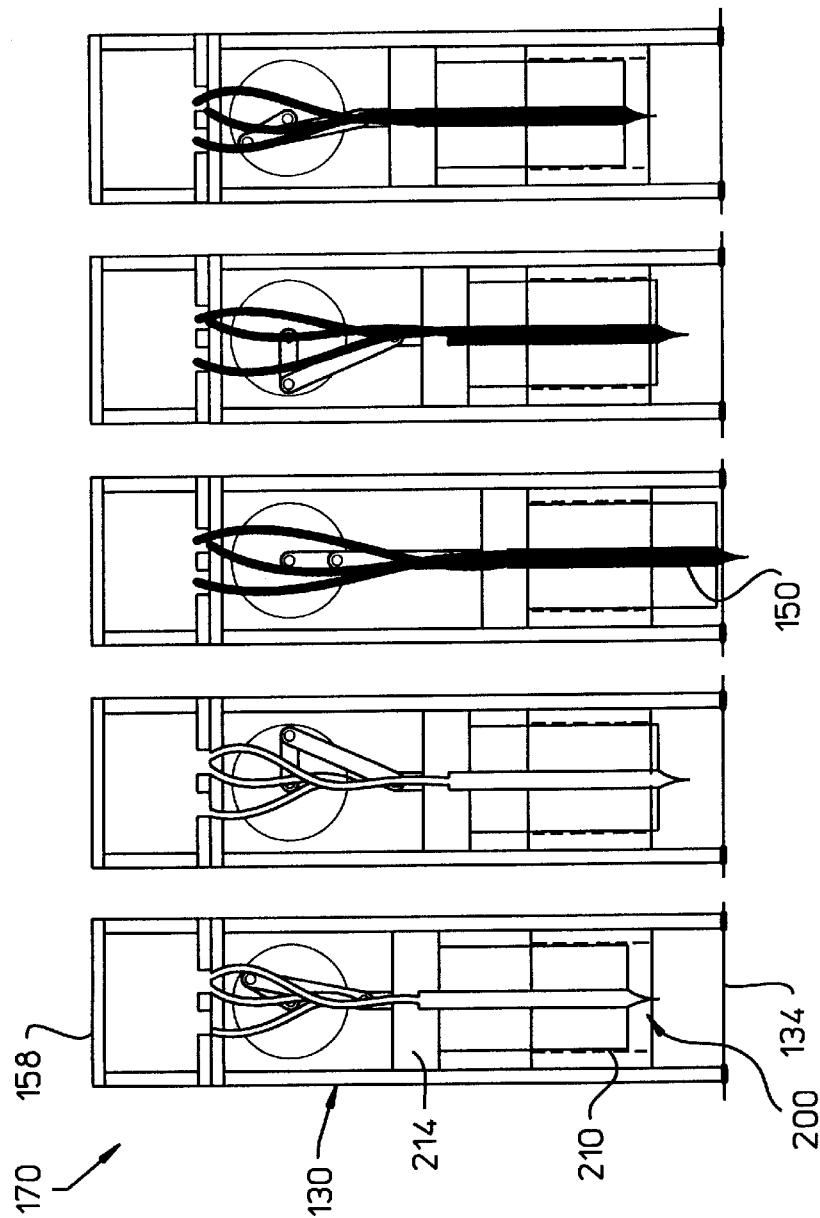

APPARATUS AND METHOD FOR MINIMALLY INVASIVE BLOOD SAMPLING

FIELD OF THE INVENTION

The present invention relates to techniques for obtaining blood samples, and more particularly to techniques for obtaining blood samples in a less painful manner.

BACKGROUND

The analysis and quantification of blood components is an important diagnostic tool for physicians. Although good noninvasive blood analysis technology is not currently available, blood samples still need to be obtained from a great number of patients every day. A well known example is home monitoring of glucose levels by a diabetic individual. Typically, such a person would prick a finger to obtain a drop of blood and then manually transfer it to an analysis strip. Unfortunately, currently available autopricking devices induce significant pain, which in turn results in low patient compliance for self testing. Much effort has been devoted to developing devices that would result in less pain in finger pricking. Pain reduction in blood sampling is believed to lead to increased patient compliance of monitoring and treatment regimens, thus improving disease management, resulting in lower long-term treatment costs.

A trend in modern blood collection methods has been to collect smaller sample volumes. Conventional blood sampling methods require a drop of blood to form on the surface of the skin, which is difficult to achieve with small incisions yielding small sample volumes. Miniaturization of the pricking element in an effort to reduce pain upon lancing, and hence generating small sample volumes, requires a compatible blood collection and storage apparatus.

(a) Mechanical Phenomenon of Skin Rupture

To successfully obtain blood, a piercing device must traverse the skin's various layers to reach the blood vasculature. Human skin is composed of a tough, keratinized squamous epithelium. The outermost layer of skin is known as the epidermis (100 microns thick), and has its own distinct layers: stratum corneum, stratum lucidum, stratum granulosum, stratum spinosum, and stratum basale. (For a review about skin, see Tortua and Anagnostakos "*Principles of anatomy and Physiology*," Harper and Row 1981). The innermost layer consists of the dermis, which is 2–5 microns thick. Because of its varying elasticity and the thickness due to the cellular structure and anatomical locations, the force necessary for penetrating the epidermis to access the vascular beds within the dermis layer will vary. It has been reported that skin tension is the greatest in the areas where the epidermal elastic keratinous fibers are dense, particularly in regions where the skin is thick, such as is found in the epigastric (stomach) regions.

The amount of force necessary to penetrate the skin surface will depend on the force applied normal to the surface of the skin needed to exceed the rupture strength. There exists an elastic range within which the degree of deflection corresponds directly with the applied force (skin depression). When the rupture limit is exceeded, a non-linear response by the skin (otherwise known as the inelastic response) occurs, corresponding to the further stretching of the skin at the point of application prior to rupture. The applied force reaches a maximum when the skin ruptures, resulting in the penetration of the object into the skin (see F. R. Shanley "*Strength of Materials*," McGraw Hill, 1957). The capillary bed under the dermis is approximately 300 to 750 microns below the outer surface of the skin in the areas of the fingers, the forearms and the stomach. Bleeding occurs when the penetration of the object reaches the capillary bed.

(b) Minimization of Pain

Pain in blood sampling due to the skin being pierced is thought to be generated through pressure waves that are built up at the site of puncture. Minimizing the incision angle of penetration, and hence pressure wave buildup, would greatly reduce the pain sensation on sampling, thereby reducing patient anxiety and the reluctance to self test.

In normal patients, an acceptable threshold for mechanically caused pain in the intact skin is 0.7 g +/−0.06 g over an area of 491 square microns, for a piercing object with a tip diameter of 25 microns (see Dash and Deshpande "*Pain and itch sensations: specific chemosensory mechanisms in the human skin*," The Somatosensory System, Theme edition/PSG 1975). A successful method to minimize pressure waves generated through skin puncture by a needle, pin or lancet, would be to minimize the area over which the puncture occurs. This can be achieved by miniaturizing the needle or lancet, provided the force applied to create the wound is small. The smaller the needle, the less force is required to puncture the skin, and less nerves endings are stimulated by the cut. In addition to the force required to penetrate the skin, the depth of penetration affects the sensation of pain as well.

Current methods for blood sampling (e.g. self testing at home) involve the cutting or slicing action of a lancet type device. The state-of-the-art sampling devices use spring-driven lancets to puncture the skin. Examples of such devices are described in Meinke (U.S. Pat. No. 4,442,836), Burns (U.S. Pat. No. 4,535,769), Morita (U.S. Pat. No. 5,314,442), and Jorgensen (U.S. Pat. No. 5,439,473). Also, O'Brien (U.S. Pat No. 4,924,879) describes a blood lancet device that results in reduced pain in blood sampling while obtaining a sufficient amount of blood through shaping of the wound. This device indexes the lancet position such that different portions of the skin are punctured on each use. It is noticeable, however, that such devices do not address the problem of significantly reducing the pain on incision as a function of wound size, as well as pressure applied. Burns (U.S. Pat. No. 5,395,387) describes a lancet assembly incorporating a cutting edge that is designed to reduce pain through an increase in the shear percentage of the blade (increase in the ratio of the length of the cutting edge to the total inserted blade length). However, such a device can still lead to significant amount of pain if an incision is made large enough to collect a large drop of blood.

One disadvantage of miniaturization of conventional lancets is fragility, which might lead to breakage of the lancet in the wound. Pain (which people universally want to avoid) is one reason for non-compliance of home blood sampling. Thus, there is a need for a blood sampling device that can be used with minimal or no pain, and yet is capable of providing and transferring an adequate amount of blood either to a test strip or to a storage area.

SUMMARY

The present invention can be used to produce an incision that can provide a blood sample with minimal or no pain. In an embodiment, the present invention provides a blood sampling device having a housing and a blade structure. The blade structure is operatively connected to the housing such that it can be extended from the housing to pierce the patient's skin, and subsequently retracted. The blade structure has at least two blades, each of which includes a cutting edge. The blades abut one another to form at least one rigid joint from which the blades extend, such that the cutting edges are remote from the rigid joint. The blade structure has a distal portion, in which the distance from the rigid joint to the cutting edge decreases towards the distal end and terminates at a sharp point. Each blade has a center plane that forms an angle less than 180 degrees with the center plane of at least one neighboring blade. The blades, joining at an angle, reduce the tendency of the blade structure to flex as the distal end of the blade is driven to penetrate the skin to yield blood.

Generally, when the thickness and width of a blade are greatly decreased, the blade becomes fragile. However, it is believed that only a penetration depth of 750 microns is required to reach the subcutaneous vasculature to obtain blood. Thus, a small sturdily constructed skin-piercing device would suffice. The unique structure of the blade systems of the present invention affords increased structural strength and integrity compared with devices such as needles. The blade structure of the present invention has reduced cross sectional area compared to conventional devices, while maintaining adequate strength and rigidity of the blade structure. To sample blood, less volume of material is being inserted into the skin to create the incision than a corresponding needle (i.e., one with a round cross section). To draw a certain amount of blood, the angled blade structures of the present invention cut with little pressure wave generation, leave a smaller incision, and produce less pain than the standard lancet. The blade structures of this invention pierce the skin with a cutting action, rather than a direct piercing action on the skin (as occurs with a conventional lancet), thereby resulting in little or no pain. Furthermore, the blade system can be incorporated into a tube for transfer of blood to a suitable storage area. Such a tube or tubes can be well protected by the blades so as to post very little interfere with the piercing action of the blades, and prevent the tube(s) from being accidentally pulled out of the skin.

BRIEF DESCRIPTION OF THE DRAWING

The following figures, which exemplify the embodiments of the present invention, are included to better illustrate the embodiments of the apparatus and use of the present invention. In these figures, like numerals represent like features in the several views.

FIG. 1A shows an isometric view of a blade structure of the present invention.

FIG. 1B shows a schematic side-view of the blade structure of FIG. 1A.

FIG. 1C shows a schematic end-view of the blade structure of FIGS. 1A and 1B.

FIGS. 3A–3E show schematic side-views of a blood sampling device of the present invention, in different stages of actuation to pierce a patient's skin.

FIGS. 4A–4E show schematic side-views of another blood sampling device, which has a plunger, in different stages of actuation to pierce a patient's skin.

FIGS. 5A–5E show schematic side-views of a blood sampling device, which has a tube for conducting blood, in different stages of actuation to pierce a patient's skin.

FIGS. 6A–6E show schematic side-views of a blood sampling device, which has a number of tubes for conducting blood, in different stages of actuation to pierce a patient's skin.

FIG. 6F shows a schematic cross-sectional view the blade structure of the blood sampling device of FIGS. 6A–6E.

FIG. 7A shows a schematic side-view of another blood sampling device, which has a blade structure made from cut-off capillaries, in different stages of actuation to pierce a patient's skin.

FIG. 7B shows in more detail a schematic side-view of the blade structure of the a blood sampling device of FIG. 7A.

FIGS. 7C–7F show schematic cross-sectional-views of the blade structure of the blood sampling device of FIGS. 7A–7B.

FIGS. 8A–8E show schematic side-view of the blood sampling device of FIG. 7 in different stages of actuation to pierce a patient's skin.

DETAILED DESCRIPTION OF THE INVENTION

Figure 2A:
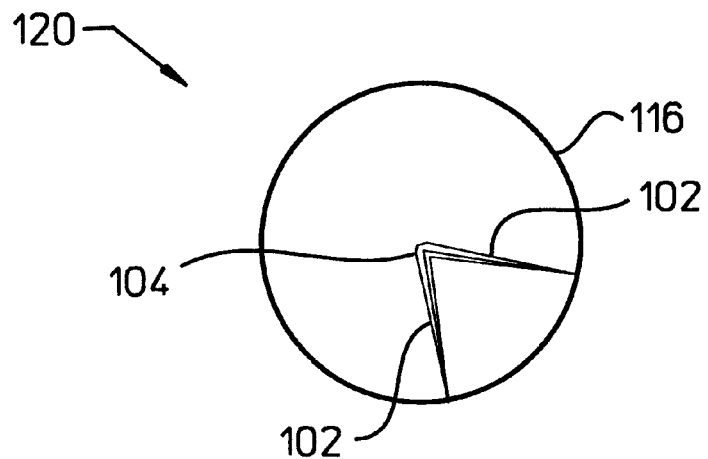
FIG. 2A shows a schematic end-view of another embodiment of a blade structure of the present invention.

The present disclosure provides a minimally invasive technique for obtaining a blood sample from the skin using a blade system. The blood sampling device has a blade structure with a least two blades abutting and supporting one another to increase strength. Each of the blades forms a non-180 degree angle (i.e., less than 180 degrees, since the complement of an angle larger than 180 degrees is one less than 180 degrees) with a neighboring blade, and includes a cutting edge. A rigid joint joining two or more blades reduces flexion and facilitates penetration.

Obtaining a Blood Sample by a Cutting-Blade System

FIG. 1 shows an embodiment of the miniature cutting structure, herein referred to as the "blade structure" of the present invention. As used herein, the term "blade structure" refers to a pricking element having a sharp point and blades, although not necessarily having only two blades or with only two cutting edges. The blade structure can be used to puncture or pierce a patient's skin to obtain a blood sample.

As shown in FIG. 1A (an isometric view), the blade structure 100 has a plurality of blades (in this case three) 102. The blades 102 can be made of conventional lancet material such as steel. The blade structure 100 resembles an arrow tip with three blades. FIG. 1B shows a schematic side view and FIG. 1C shows a schematic end-view of the blade structure 100. Angle "a," the "blade angle," is the angle the cutting edge 108 makes with the rigid joint 104. The three blades 102 abut and join together at the rigid joint 104 such that the blades extend from the rigid joint in a radial pattern. Each of the blades 102 forms an angle of about 120 degrees with its neighbors. It is noted that as used herein, the term "rigid joint" refers to a structure where the blades are affixed together. The rigid joint may simply be the joint formed by the blades affixedly meeting one another. The rigid joint can be a shaft having a size (e.g., diameter) larger than the thickness of the blades for added support, analogous to the hub of a wheel.

The tip of such a blade structure terminates at a sharp point at its distal end to facilitate the initiation of penetration. As used herein the term "distal" refers to the direction of the blade structure extending towards the patient. The term "proximal" refers to a direction opposite to the distal direction (away from the sharp point of the blade structure). Each of the blades 102 has a cutting edge 108 being remote from the rigid joint 104.

At the distal portion 110, the distance from the rigid joint 104 to each of the cutting edges 108 decreases gradually towards the distal end 112 such that the three blades 102 terminate at a sharp point 114. Proximally, the blades 102 can terminate and be supported by a support 116 to reduce freedom of movement of the blades, thereby strengthening them. Additionally, the rigid joint 104 helps to strengthen the blades 102 to reduce their tendency to flex when the blade structure 100 is puncturing the patient's skin.

Figure 2B:
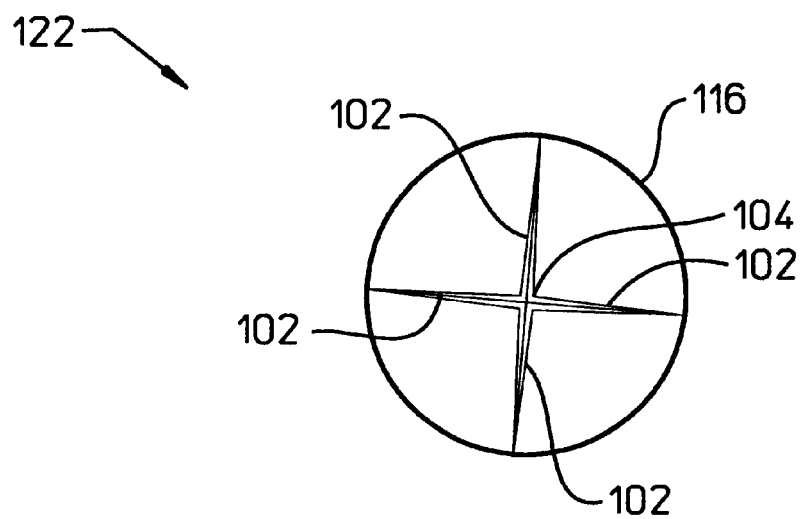
FIG. 2B shows a schematic end-view of yet another embodiment of a blade structure of the present invention.

FIG. 2A shows a schematic end-view of another embodiment of a blade structure of the present invention. Instead of having three blades as in FIG. 1, the blade structure 120 has two blades 102, arranged to form a non-180 degree angle. In fact, in this embodiment, the smallest angle between the blades 102 is less than 180 degrees (moreover, it is an acute angle). Preferably, for an embodiment with two blades, the angle between the neighboring blades is a right angle or less than 90 degrees. FIG. 2B shows a schematic end-view of another embodiment of a blade structure 122 of the present invention having four blades 102 abutting and joining together at right angles. It is contemplated that more than four blades can be joined to make a blade structure of the present invention, although, due to the complexity of the manufacturing process, this would be less preferred. Thus, the preferred blade structure has two to five blades, more preferably has three to four blades.

To facilitate penetration of the blade structure of the present invention into skin, the preferred blade angle, a, is between 15 and 20 degrees. Such a blade angle results in a large shear percentage (for definition, see, e.g., Burns, U.S. Pat. No. 4,230,118) and will provide sufficient distance of travel for shearing with minimal pain by the blades to produce a wound of suitable size. Preferably, the blades 102 are thicker near the rigid joint 104 and gradually (though not necessarily with a uniform gradient) become thinner towards the cutting edge 108. The blades 102 would have a thickness less than 100 microns near the distal portion of the cutting structure to enter the patient's tissue, enabling them to produce very narrow, short (as viewing the skin surface from its normal, i.e. perpendicular direction) cuts. As the blades 102 penetrate the skin, they can cut with an incising action similar to that of a scalpel, thus reducing tearing and trauma to the skin.

The embodiments described herein can be used to obtain less than 50 microliters of blood sample and thus, by miniaturization of the blade structure while maintaining structural strength, significantly reduce pain associated with lancing the skin. In addition, including angled blades having cutting edges with a large shear percentage will also reduce pain associated with skin puncture. In the case of the blade structure 100 shown in FIG. 1, the wound is similar in appearance to the symbol of a star with three points. The maximum depth of the blade penetration can be limited to not exceed a preset value, e.g., 500 microns. For example, this can be accomplished by affixing a stopping pin on each blade or on a guiding block that limits the movement of the blades.

FIG. 3 shows an embodiment of a blood sampling device (or blood sampler) 124 of the present invention, with an actuator 126 for driving the cutting motion of a blade structure 128, i.e., for penetration into a tissue such as skin. An example of a blade structure for this device is the blade structure of FIG. 1. A housing 130 (here shown in cross-section) encloses the blade structure 128, except at its distal end, which has an opening 132 for receiving blood from the patient's skin. The embodiment of an actuator 126 shown in FIG. 3 has a cam 136, and pivotal arms 138, operatively connected to the blade structure 128. Rotation of the cam 136 drives the cam rod and pivotal arms 138 to move the blade structure 128 longitudinally, i.e., in the proximal-distal directions of the rigid joint of the blade structure 128. FIG. 3A shows the position of the blade close to the most retracted mode. FIG. 3B shows the blade structure 128 being extended towards the skin 134 in a plunger-like motion. FIG. 3C shows the blade structure 128 penetrating the skin 134 (only the surface of the skin is shown in the figure). An optional tube-like stabilizer 140 with a lumen 143 is connected to the housing 130 to confine the blade structure 128 and limit its lateral movement. The stabilizer 140 can be just slightly larger than the support 142 of the blade structure 128, to enable it to fit therein.

FIG. 3D shows the blade structure 128 being retracted, and FIG. 3E shows the blade structure being fully extended. The maximum depth of penetration of this blood sampling device 124 is set by the physical length of the cam rods and pivotal arms 136. The actuator quickly forces the blades into the skin, and retracts them from the wound area. Thus, both the contact time and amount of surface area exposed during puncture can be reduced.

Preferably the housing 130, containing the actuator 124 and the blade structure 128, also serves to aid in the extraction of blood. The open end of the housing 130 touches the skin 134, and forms a tight gripping seal with the skin. Preferably the housing 130 can be made deformable such that when the blade structure 128 is driven towards the skin, the opening 132 of the housing 130 expands slightly so as to stretch the skin taut momentarily as the blade structure 128 penetrates. When the blade structure 128 begins to retract, the backward motion also produces a slight sucking action to draw a sufficient blood into the chamber for storage. Alternatively, capillary action can provide the primary force to draw the blood up into the housing 130.

FIG. 4 shows an embodiment of a blood sampling device 146 similar to that of FIG. 3, but with a plunger 148 which slides in the housing 130 in such a manner that the plunger makes a sliding seal with the housing.

FIGS. 4A, 4B, 4C, 4D, 4E show the actuation of the blade structure 128 in a manner similar to that shown in FIG. 3, including extension and retraction of the blade structure. After skin penetration (FIG. 4C), the retraction of the blade structure 128 and plunger 148 creates a suction to draw blood 150 into the chamber 144 (FIGS. 4D and 4E).

FIG. 5A shows a blood sampling device 152 having a center tube 156 (e.g., capillary) in the middle of the blade structure 128. The blood sampling device 152 has the actuator, housing, and stabilizer similar to those of FIGS. 3 and 4. Preferably the distal end of the tube is shaped with an angle to conform to the cutting edges 108, and become a complete tube proximally along the length of the blade structure. The lumen of the tube can transfer fluid such as blood to an optional sample storage chamber 158. The tube has an inner diameter (i.d.) large enough to allow blood (fluid) extraction.

To use the blood sampling device 152 for sampling and for storage of blood (e.g., with suction and space for storage), the blade structure 128 is driven to penetrate and allowed to remain in the wound site long enough to fill the chamber via the lumen of the tube 156 (e.g., by suction). The sample tube may need to be precoated with an anti-coagulant or preservative 157 prior to use.

Once the skin has been pierced, an efficient way to transfer blood from the incision site to a storage area is important both for reducing the risk of dislodging the needle during the sampling period, as well as minimizing pain. An efficient mechanism for removing blood from the incision site would be through capillary forces. Capillary forces are responsible for sample chamber filling in modern glucose testing devices. Sample volumes required for sensor strip scanning are in the order of a few (e.g. 4) microliters.

Filling a 10 microliter glass capillary of 500 microns diameter to a column height of 30 mm by capillary action takes less than one second. The tube 156 can therefore be a capillary, preferably with an inside diameter (I.D.) between about 100 microns (0.004 in) and 650 microns (0.025 in), more preferably between about 200 microns (0.008 in) and 400 microns (0.016 in) for optimal volume of fluid that can be transferred in the capillary.

The blade structure 128 penetrates and remains in the wound site for a pre-determined (preset) length of time, long enough for capillary forces to pull fluid into the capillary. Once this pre-determined time has expired, the actuator retracts the blade structure from the skin. The distal portion of the capillary, cradled (preferably snugly) at the middle of the blade structure 128, can be a hypodermic needle. Using a conventional hypodermic needle for this purpose means that there will be a minimum gauge that is manufacturable, while also small enough to minimize pain. The wall thickness will determine the surface area penetrating the skin as well as the failure strength of the needle itself.

FIG. 6 shows a blood sampling device 160 having a plurality of capillaries 162, for the extraction of blood, and a blade structure 128. Although only three capillaries and three blades are shown, a person skilled in the art will understand that other numbers of blades and capillaries can be implemented. The troughs (or cavities) formed by the multiple blades 164 abutting at an angle provide additional support for the capillaries, which nestle in the troughs. This configuration enables the use of rigid bio-compatible polymers such as polyimide rather than requiring metallic materials such as stainless steel for the manufacture of the capillaries. As shown in the cross sectional view of FIG. 6F, the three capillaries 156 are interposed with the three blades 164 of the blade structure 128. An actuator, such as a cam, or spring loaded mechanism, can be used to drive the blade structure 128 in the distal direction (FIGS. 6A, 6B) and forces the blades to pierce the skin 134 (FIG. 6C). At the same time the capillaries move with the blade structure 128 until the distal tips of the capillaries are near the surface of the skin, co-located with the incision. As the blades 164 make the incision and reach full stop, blood flows from the incision and enters the capillary tip 168, which remains near the surface of the skin 143 (FIG. 6C). Capillary forces draw the blood into the lumen of the capillaries. When the blades 164 retract into the protective housing 130, the capillary tip 168 remains at the skin 134 and continues to extract blood into the capillaries 162.

FIG. 7 and FIG. 8 show another embodiment of a blood sampling device 170 of the present invention. FIG. 7A shows the general structures, FIG. 7B shows the details of the capillaries near the distal tip, and FIGS. 7C, 7D, 7E and 7F show the cross-sectional views of the blade structure 200 at different positions along the axis (or center line) of the blade structure. In these figures the blade structure 200 is formed by the edges formed by cutting three neighboring capillaries 202A, 202B, and 202C (see FIG. 7B). The distal portion of the three capillaries 202A, 202B, 202C are effectively stabilized by being affixed together into a single structure, e.g., with adhesive, melting, or welding. In the blade structure 200, the capillaries have been cut and shaped in such a way that their walls form curved edges. FIG. 7D shows the cutting edges 208A, 208B, and 208C. The dotted lines show the cut away portions of the capillaries such that the cutting edges 208A, 208B and 208C can be formed. In the blade structure 200, farther away from the tip 207 beyond the region of the cutting edges 208A, 208B and 208C, the three capillaries are joined in a simple closely packed triangular structure (FIG. 7C). Each of the capillaries, when obliquely cut, forms an arc 209 in the cross-sectional view. Each arc 209 can be bisected by an imaginary center plane 211 (see FIG. 7F). Thus, the center planes 211 for the three cut capillaries each form an angle about 120 degrees with each of its neighboring planes. Any two neighboring arcs 209 join to form a cutting edge, resulting in the cutting edges 208A, 208B and 208C. Near the distal tip, a central pin 206 strengthens the capillaries and facilitates entry into a patients skin (FIG. 7E).

The small diameters of the three capillaries enable the blade structure 200 to inflict less pain at penetration than a blade structure having tubes of the same diameter in a structure as that of FIG. 6. If the capillaries are made out of semi-flexible polymer such as polyimide, either a central pin (FIG. 7E) or a reinforced surface coating (such as a diamond film coating) can be used to stiffen the blade structure 200, to facilitate penetration into the skin. Capillary forces draw blood into the sampling device 170. FIG. 8 shows the operation of the blood sampling device 170. The blood sampling device 170 has a stabilizer 210 that stabilizes the blade structure 200 from excessive lateral movement. FIGS. 8A, 8B, 8C, 8D, and 8E show how the blade structure 200 is driven by the actuator to extend towards, and retract from, the patients skin, in a manner similar to FIGS. 3, 4, 5, and 6.

Sample Storage, Transfer and Analysis

A closed sample compartment will reduce fluid losses due to evaporation, as well as prevent contamination from other sources, such as air borne particulates. In addition, for larger sample volumes, some substances or agents for stabilizing the blood (such as citrate, heparin, cooling, etc.) can be included in the sample chamber if analysis does not follow acquisition immediately. Such stabilization techniques avoid sample alteration due to biological processes such as clotting. Preferably, the sample storage chamber or compartment itself is detachable from the housing of the blood sampling device for the direct transport to the site of analysis. The sample storage chamber can also have a universal fitting, which can connect to whatever sampling device or port used. The ability to disconnect the sample chamber from the body of the acquisition cutting device (i.e., the blade structure) allows safe disposal of the acquisition cutting device, thus reducing the risk of contamination. For micro-sample analysis, the storage chamber can be modified for on-board analysis to reduce sample loss due to evaporation or spillage. The device would then be a disposable acquisition-and-analysis module for targeted analyte analysis.

Some of the sensors on the skin have a tendency to adapt to their stimuli after some time, ceasing transmission of signals. To make use of this fact to reduce discomfort further, it may be possible to employ additional nerve-stimulation techniques to distract the patient from the perception of pain resulting from the trauma caused by sampling blood. Although the illustrative embodiments of the device of the present invention and the method of making and using the device have been described in detail, it is to be understood that the above-described embodiments can be modified by one skilled in the art, especially in sizes and shapes and combination of various described features without departing from the scope of the invention.

What is claimed is:

1. A blood sampling device for penetrating skin to sample blood therefrom, comprising:
 (a) a housing;
 (b) a blade structure retractably connected in the housing, the blade structure having at least two blades each including a cutting edge, the blades abutting one another to form one or more rigid joints such that the cutting edges are remote from the corresponding one or more rigid joints, the blade structure having a distal portion in which for each blade the distance from the rigid joint to the cutting edge associated with the blade decreases towards a distal end of the blade structure, to terminate at a sharp point, such that a plane that passes through the mid-line of a blade (center plane) forms an angle less than 180 degree with at least one neighboring center plane of blades neighboring thereto, thereby decreasing the tendency of the blade structure to flex as the distal end of the blade structure is driven into the skin to yield blood therefrom;

(c) means connecting to the blade structure and the housing for limiting the penetration of the blade structure to a distance in the skin sufficiently deep to cause bleeding.

2. The blood sampling device according to claim 1 wherein the blades are planar and extend radially from the rigid joint.

3. The blood sampling device according to claim 2 further comprising at least one capillary, the capillary extending along the rigid joint at the distal portion of the blade structure and being cradled between two blades that abut at an angle less than 180 degrees, the capillary having a distal opening proximate to the distal end of the blade structure.

4. The blood sampling device according to claim 3 wherein the capillary is detachable at least in part from the distal portion of the blade structure such that after penetrating the skin the blade structure is retractable from the skin, thereby leaving the distal opening of the capillary to stay proximate to the skin for allowing blood to enter the capillary therefrom.

5. The blood sampling device according to claim 3 wherein the blade structure has three or more planar blades and the same number of capillaries as the blades, each capillary being cradled between two blades forming an angle between 70 degrees and 120 degrees.

6. The blood sampling device according to claim 2 wherein the housing has an annular wall surrounding a distal opening to a chamber in the housing from which the distal end of the blade structure can protrude to penetrate the skin, such that blood can enter through the distal opening to the chamber after the blade structure is retracted from the skin.

7. The blood sampling device according to claim 1 wherein the blades are adapted to have arc surfaces such that cross sections of the distal portion of the blade structure vary in shape dependent on the distance from the distal end, each cross section including abutting arcs with their arc-tips generally facing away from the mid point of the cross section, the arcs in the cross sections increasing in length progressively from a rigid point at the distal end to become shaped as a continuous ring at a location more remote from the distal end such that the blades change progressively from a point at the distal end to each become a capillary through which blood can pass at the location more remote from the distal end.

8. The blood sampling device according to claim 1 further comprising an actuator associated with the blade structure for driving the blade structure and retracting the distal end of the blade structure into the housing, the device further comprising a means associated with the housing proximate to the blade structure for accepting blood after the blade structure incises the skin.

9. The blood sampling device according to claim 1 wherein the cutting edges have no sharp bends to penetrate the skin.

10. The blood sampling device according to claim 1 further comprising a suction means for removing blood from the skin after incision by the blade structure.

11. The blood sampling device according to claim 1 wherein at least three blades abut one another in the blade structure.

12. A blood sampling device for penetrating skin to sample blood therefrom, comprising:

(a) a housing;

(b) a blade structure operatively retractably connected to the housing, the blade structure having three planar blades each including a cutting edge, the blades abutting one another to form a rigid joint from which the blades extend such that the cutting edges are remote from the rigid joint, the blade structure having a distal portion in which the distance from the rigid joint to each cutting edge decreases towards a distal end terminating at a sharp point, each blade forming an angle less than 180 degrees with blades neighboring thereto;

(c) one to three capillaries, each capillary extending along the rigid joint at the distal portion of the blade structure and being cradled between two blades, each capillary having a distal opening proximate to the distal end of the blade structure for blood to enter from the skin; and (d) an actuator associated with the blade structure for driving the blade structure to incise the skin and retracting the distal end of the blade structure into the housing after incision.

13. A method of making a blood sampling device for penetrating skin to sample blood therefrom, comprising:

installing a blade structure in a housing in such a way that the blade structure is extendable out of the housing and retractable into the housing, the blade structure having at least two blades each including a cutting edge, the blades abutting one another to form one or more rigid joints such that cutting edges are remote from the corresponding one or more rigid joints, the blade structure having a distal portion in which for each blade the distance from the rigid joint to the cutting edge associated with the blade decreases towards a distal end of the blade structure to terminate at a sharp point, such that a plane that passes through the mid-line of a blade (center plane) forms an angle less than 180 degrees with at least one neighboring center plane of blades neighboring thereto, thereby decreasing the tendency of the blade structure to flex as the distal end of the blade structure is driven into the skin to yield blood therefrom.

14. The method according to claim 13 further comprising disposing at least one capillary in the blood sampling device such that each of the at least one capillary extends along the rigid joint at a distal portion of the blade structure and is cradled between two blades that abut at an angle, the capillary having a distal opening proximate to the distal end of the blade structure.

15. The method according to claim 14 further comprising detachably disposing at least a portion of the at least one capillary on the blades such that after penetrating the skin the blade structure can be retracted from the skin to leave the distal opening of the capillary proximate to the skin to pass blood into the capillary.

16. The method according to claim 14 wherein the angle between adjacent blades is between 70 degrees and 120 degrees.

17. The method according to claim 13 wherein the rigid joint has a center and the method further comprising attaching nonplanar blades to form the blade structure, such that the cross sections of the distal portions of the blades form arcs having arc-tips facing away from the center of the rigid joint, the arcs increasing in length progressively from the distal end to become circular remote from the distal end such that the blades each become a capillary through which blood can pass.

18. The method according to claim 13 further comprising installing an actuator to associate with the housing for driving the distal end of the blade structure out of and back into the housing and further comprising installing a means associated with the housing proximate to the blade structure for accepting blood after the blade structure cuts the skin.

19. A method for sampling blood from skin, comprising:

driving a blade structure from a housing to penetrate the skin, the blade structure having at least two blades each including a cutting edge, the blades abutting one another to form a rigid joint from which the blades extend such that the cutting edges are remote from the rigid joint, the blade structure each having a distal portion in which the distance from the rigid joint to the cutting edge decreases towards a distal end to terminate at a sharp point, each blade having a center plane such that each center plane forms an angle less than 180 degrees with at least one neighboring center plane of blades neighboring thereto, such that the tissue of the skin slides along the surface of the blades to reduce tearing and such that the tendency of the blade structure to flex is reduced as the distal end of the blade structure is driven into the skin to yield blood therefrom;

stopping the blade structure after the blade structure has penetrated the skin to a distance reaching blood vessels to cause bleeding; and withdrawing the blade structure from the skin to allow blood to exit the skin.

20. A blood sampling device for penetrating skin to sample blood therefrom, comprising:

(a) a housing; and (b) a lancet size blade structure retractably connected in the housing, the blade structure having at least two blades each including a cutting edge, the blades abutting one another to form one or more rigid joints such that the cutting edges are remote from the corresponding one or more rigid joints, the blade structure having a distal portion in which for each blade the distance from the rigid joint to the cutting edge associated with the blade decreases towards a distal end of the blade structure, to terminate at a sharp point, such that a plane that passes through the mid-line of a blade (center plane) forms an angle less than 180 degree with at least one neighboring center plane of the neighboring blades neighboring thereto, thereby decreasing the tendency of the blade structure to flex as the distal end of the blade structure is driven into the skin to yield blood therefrom.

21. The blood sampling device according to claim 20, wherein each blade in the blade structure has a thickness that is less than 100 microns near the distal portion.

22. A blood sampling device for penetrating skin to sample blood therefrom, comprising:

(a) a housing; and (b) a blade structure retractably connected in the housing, the blade structure having at least two blades each including a cutting edge, the blades abutting one another to form one or more rigid joints such that the cutting edges are remote from the corresponding one or more rigid joints, the blade structure having a distal portion in which for each blade the distance from the rigid joint to the cutting edge associated with the blade decreases towards a distal end of the blade structure, to terminate at a sharp point, such that a plane that passes through the mid-line of a blade (center plane) forms an angle less than 180 degree with at least one neighboring center plane of blades neighboring thereto, thereby decreasing the tendency of the blade structure to flex as the distal end of the blade structure is driven into the skin to yield blood therefrom; wherein the blades are generally planar and extend radially from the rigid joint; and (c) at least one capillary, the capillary extending along the rigid joint at the distal portion of the blade structure and being cradled between two blades that abut at an angle less than 180 degrees, the capillary having a distal opening proximate to the distal end of the blade structure.

* * * * *